United States Patent [19]

Chanock et al.

[11] Patent Number: 4,927,628

[45] Date of Patent: May 22, 1990

[54] VACCINE AGAINST ROTAVIRUS DISEASES AND METHOD OF PREPARING SAME

[75] Inventors: Robert M. Chanock, Bethesda; Albert Kapikian, Rockville, both of Md.; Karen Midthun, Washington, D.C.; Jorge Flores, Bethesda, Md.; Mario Gorziglia, Silver Spring, Md.; Yasutaka Hoshino, Bethesda, Md.; Irene Peres-Schael, San Jose, Venezuela

[73] Assignee: The United States of America as represented by the Department of Health and Human Services, Washington, D.C.

[21] Appl. No.: 98,977

[22] Filed: Sep. 21, 1987

[51] Int. Cl.$^5$ ............... A61K 39/12; C12N 15/00; C12N 7/00

[52] U.S. Cl. ............... 424/89; 424/90; 424/86; 435/172.3; 435/235; 435/236; 435/237; 435/239; 435/948

[58] Field of Search ............ 435/235, 236, 237, 172.3; 424/86, 93, 89, 90

[56] References Cited

U.S. PATENT DOCUMENTS

| | | | |
|---|---|---|---|
| 4,341,763 | 7/1982 | Zygraich | 435/236 |
| 4,341,870 | 7/1982 | Wyatt et al. | 435/237 |
| 4,571,385 | 2/1986 | Greenberg et al. | 435/236 |
| 4,624,850 | 11/1986 | Albert et al. | 435/235 |
| 4,636,385 | 1/1987 | Plotkin et al. | 424/89 |
| 4,704,275 | 11/1987 | Wyatt et al. | 435/235 |

FOREIGN PATENT DOCUMENTS 8500184  1/1985  PCT Int'l Appl. ............... 435/236

OTHER PUBLICATIONS

Greenberg et al., J. Gen. Vir., 64, 313-20, (1983).
Hoshino et al., PNAS(U.S.A.), 82, 8701-04, Dec. (1985).
Greenberg et al., J. Virology, 47(2), 267-75, (1983).
Flores et al., Infect. Imm., 37(2), 648-55, (1982).
Kalica et al., Virology, 125, 194-205, (1983).
Midthun et al., J. Virol., 53(3), 949-54, (1985).
Vesikari et al., Lancet, 2, Oct. 8, (1983), 807-11.

*Primary Examiner*—Margaret Moskowitz
*Assistant Examiner*—Jeff P. Kushan
*Attorney, Agent, or Firm*—Mishrilal Jain

[57] ABSTRACT

A new method for producing live, attenuated rotavirus strains suitable for preparing a vaccine is described. It is demonstrated that a naturally attenuated rotavirus recovered from newborns or other individuals whos have undergone asymptomatic infection can be used for immunization or that a virulent rotavirus can be converted into an attenuated strain by substituting the conserved fourth rotavirus gene segments of a naturally attenuated rotavirus in the genome of the virulent rotavirus.

2 Claims, 6 Drawing Sheets

Wa probe

DS1 probe

M37 probe

ST3 probe

```
Host
species  Strain  Virulence  Serotype         Conserved
                                              region 1
                                                                                   L                              T
                                                           G                       L                              
                                                         V G                       V                              
                                                       S V G                       SW                K
Human    VA70       +          4              MASLIYRQLLTNSYSDLHDEIEQIGSEKTQNVTINPSPFAQTRYAPVNWGHGEINDSTTVEPILDGPYQPTTFTPPNDY 80
         P          +          3
         DS1        +          2
         Wa         +          1              MASLIYRQLLTNSYSVELSDEINTIGSEKTQNVTINPGPFAQTNYAPVVLESWEVNDSTTIEPVLDGPYQPTSKPPSDY
         M37        −          1                             T        S
         1076       −          2                             T        S
         McN        −          3                             T        S
         ST3        −          4                                      I
Simian   SA-11      ?          3              ---LIYRQLLTNSYTVELSDEIQEIGSTKTQNVTVNPGPFAQTNYAPVNWGPGETNDSTTVEPVLDGPYQPTTFNPPVSY 80
         RRV        +          3              MAS              D                    I L    G                        S      D Variable region
                                                                                 T                  NT         F   I
                                                               D             V       N         D              F T TG GN S
                                                               D            SSV    SQTN     IL   N       END       FT TG GN S
                                                              ND           WILINSNTNGVVYESTNNSEFWTAVVALEPHVNPVDRQYLIFGE*SKQFNVSNDSNKWKFLEMFRSSSQNEFYNRRTLTS 159
Human    VA70       +          4              
         P          +          3
         DS1        +          2              L  S
         Wa         +          1              WILLNPTDQQVVLEGTNKTDIWIALLLVEPNVTNQSRQYTLFGE*TKQITVENNTNKWKFFEMFRKNVSAEFQHKRTLTS
         M37        −          1                  N                V                                          SS
         1076       −          2                  N                V                                          SS
         McN        −          3                  N                                                           SS
         ST3        −          4                                                                              SS  S
Simian   SA-11      ?          3              WMLLAPTNAGVVVEGTNNTNRWLATILIEPNVQQVERTYTLFGQQVQVTSNDSQTKWKFVDLSKQTQDGNYSQHGSLLS 160
         RRV        +          3              A           D       VVA   TSET S    TEI IAA  Q   IVV S  N S    Y P Q
```

FIG.5-1

| Host species | Strain | Virulence | Serotype | | |
|---|---|---|---|---|---|
| | | | | | Conserved region 2 |
| | | | | | S |
| | | | | | N S |
| Human | VA70 | + | 4 | | L |
| | P | + | 3 | | L |
| | DS1 | + | 2 | SN L M | N |
| | Wa | + | 1 | DTRFVGILKYGGRVWTFHGETPRATTDSSSTANLNNISITIHSEFYIIPRSQESKCNEYINNGLPPIQNTRNVVPLPLSS 239 |
| | M37 | − | 1 | DTKLAGFLKHYNSVWTFHGETPHATTDYSSTSNLSEVETVIHVEFYIIPRSQESKCVEYINTGLPPMQNTRNIVPVALSS 240 |
| | 1076 | − | 2 | F Y A N |
| | McN | − | 3 | T |
| | ST3 | − | 4 | S T |
| Simian | SA-11 | ? | 3 | TPKLYGVMKHGGKIYTYNGETPNANTGYYSTTNFDTVNMTAYCDFYIIPLAQEAKCTEYINNGLPPIQNTRNIVPVSIVS |
| | RRV | + | 3 | N VT K Y S F REE ST LALSA |

| Host species | Strain | Virulence | Serotype | | |
|---|---|---|---|---|---|
| | | | | | Conserved region 3 |
| | | | | | Q Y |
| Human | VA70 | + | 4 | | Q G |
| | P | + | 3 | | TI Q |
| | DS1 | + | 2 | | TI |
| | Wa | + | 1 | RSIQYKRAQVNEDIIVSKTSLWKEMLYNRDIIIRFKFGNSI 280 |
| | M37 | − | 1 | RSVTYQRAQVNEDIIISKTSLWKEMQCNRDIIIRFKFNNSI 281 |
| | 1076 | − | 2 | Y |
| | McN | − | 3 | A Y |
| | ST3 | − | 4 | Y |
| Simian | SA-11 | ? | 3 | RNIVYTRAQPNQDIVVSKTSLWKEMQYNRDIVIRFKFANSI |
| | RRV | + | 3 | T H A E T S |

FIG. 5-2

VACCINE AGAINST ROTAVIRUS DISEASES AND METHOD OF PREPARING SAME

BACKGROUND OF THE INVENTION

1. Technical Field

The present invention is related generally to vaccines against rotavirus diseases. More particularly, the present invention is related to a method of preparing a vaccine against rotavirus diseases comprising producing a pure inoculum of live rotavirus, attenuated either naturally or through reassortment, said attenuated rotavirus having in the genome thereof the fourth rotaviral gene segment with a nucleotide sequence associated with naturally attenuated human rotaviruses.

2. State of the art

It is generally recognized that there is a need for rotavirus vaccine in both the developed and developing countries. (Kapikian, et al. Rev. Inf. Dis. (1980), 2:459-469). The importance of rotaviruses as a cause of severe diarrhea in developed countries has been highlighted in numerous cross-sectional studies of infants and young children admitted with diarrheal diseases to the hospital. (Kapikian, et al. Rev. Inf. Dis. (1980) 2:459-469). For example, in a period exceeding eight years (January 1974–July 1982) rotaviruses were detected in feces of 34.5% of 1,537 patients admitted with diarrhea to The Childrens Hospital National Medical Center in Washington, D.C., (Brandt, et al. J. Clin Microbiol. (1983), 18:71-78), and in a Japanese study extending between 1974 and 1981, 45% of 1,910 pediatric patients admitted with diarrhea shed rotavirus. It is obvious from these and various other cross-sectional studies in developed countries that rotaviruses are indeed the major known etiologic agents of severe infantile gastroenteritis requiring hospitalization.

U.S. Pat. Nos. 4,624,850; 4,571,381; 4,190,645; 4,341,870; 4,341,763 and 4,205,131 describe a variety of rotavirus vaccines and/or methods of preparing the same. Other rotaviruses such as bovine rotavirus strains NCDV and WC3, and rhesus rotavirus strain MMU 18006 have also been studied. However, a vaccine comprising live attenuated human rotavirus strain which possesses, either naturally or through genetic reassortment technology, a highly conserved fourth viral gene segment, has not heretofore been suggested or employed as means for inducing immunity against rotavirus diseases without producing unacceptable pathological side effects in the susceptible host.

SUMMARY OF THE INVENTION

It is, therefore, an object of the present invention to provide an improved vaccine against rotavirus diseases.

It is a further object of the present invention to provide a method for producing a rotavirus vaccine utilizing naturally attenuated or reassortant rotavirus strains in which the conserved fourth viral gene segment of naturally attenuated human rotaviruses is present in the viral genome.

Various other objects and advantages of the present invention will become evident from the Detailed Description of the Invention.

BRIEF DESCRIPTION OF THE DRAWINGS

These and various other objects, features, and many of attendant advantages of the invention will be better understood upon a reading of the following detailed description when considered in connection with the accompanying drawings wherein:

FIG. 5 shows a comparison of the amino acid sequence of VP8, the cleavage sites and N terminus of VP5 of four virulent (+) and four asymptomatic (−) human rotaviruses. The conserved and variable regions are indicated by overline; *, insertion or deletion; —, region of DNA for which the sequence has not been determined; ↓, cleavage site; ▼, possible alternate cleavage site. Note that the sequence of SA-11 and RRV is presented for purpose of comparison.

DETAILED DESCRIPTION OF THE INVENTION

Figure 1:
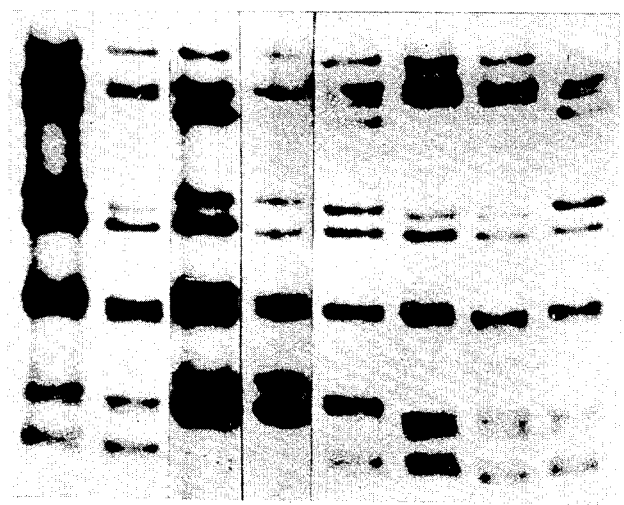
FIG. 1 shows autoradiogram of Northern blot hybridization at a higher stringency (52° C., 50% formamide, 2.5×SSC) of $^{32}$P-labeled virulent human rotavirus Wa (top) and virulent human rotavirus DS1 (bottom) ssRNA probes to denatured genomic RNAs from the following rotavirus strains immobilized on DBM membranes after PAGE: lane 1, WA; lane 2, asymptomatic neonatal M37; lane 3, DS1; lane 4, asymptomatic neonatal 1076; lane 5, virulent human rotavirus P; lane 6, asymptomatic neonatal rotavirus McN; lane 7, asymptomatic neonatal rotavirus ST3; lane 8, virulent human rotavirus VA70. o identifies strains recovered from asymptomatic newborn infants. Lanes 3 and 4 (top) were exposed for a longer period of time.
Figure 1:
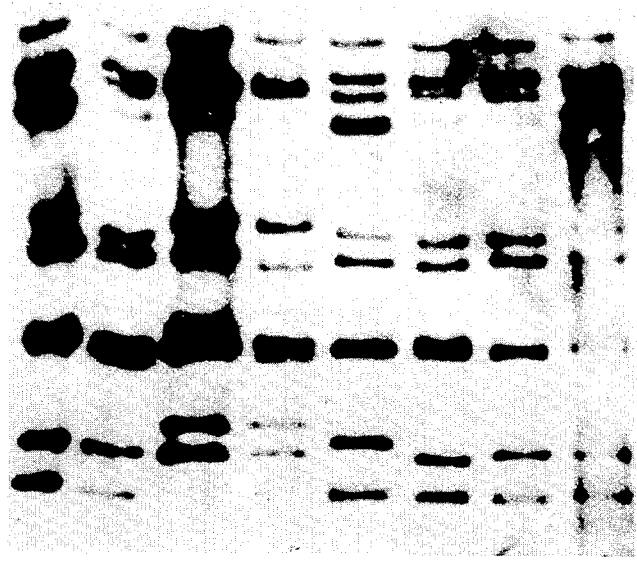

The above and various other objects and advantages of the present invention are achieved by a vaccine against rotavirus diseases comprising live attenuated human rotavirus strain(s) or reassortants thereof having present in the viral genome at least the conserved fourth viral gene segment of naturally attenuated rotavirus and a method of producing the same.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

MATERIALS AND METHODS

Strains:

The following strains isolated from asymptomatic newborn infants were studied: M37, a subgroup 2, serotype 1 strain from Venezuela (Perez-Shael, et al (1984) *J. Med. Virol.* 14:127-136); 1076, a subgroup 1, serotype 2 strain from Sweden; McN, a subgroup 2, serotype 3 strain from Australia (Bishop et al, *J. Clin. Microbiol.* 24:1023-1028, 1986); ST3, a subgroup 2, serotype 4 strain from England (Chrystie, et al, (1975) *Lancet* ii:79).

Four well-characterized laboratory strains, originally isolated from ill infants or children, were also studied: Wa, subgroup 2, serotype 1 (Wyatt, et al, (1983) *Science* 207:189-191); DS1, subgroup 1, serotype 2, (Wyatt, et al (1983), *J. Clin. Microbiol.* 18:310-317); P, subgroup 2, serotype 3, (Wyatt supra.),; and VA70, subgroup 2, serotype 4 (Gerna, et al. (1984) *J. Clin. Microbiol.* 19:273-278). The first three of these strains (Wa, DS1, and P) were isolated in Washington, D.C.; VA70 was isolated from a child in Italy.

Each of the rotavirus strains studied was grown in MA-104 cells in the presence of trypsin (0.5 ug/ml), and virions were purified as described by Flores, et al (1982) *J. Virol.* 43:1032-1037.

It is noted that RNA-RNA hybridization was used to assess the genetic relatedness of different rotavirus strains isolated from asymptomatic newborn infants in hospital nurseries and to compare these strains with rotaviruses isolated from symptomatic infants and young children.

RNA extraction and preparation of probes:

Single-shelled particles were extracted twice with phenol and once with chloroform to obtain genomic double-stranded (ds) RNAs. Single-stranded (ss) RNA probes (mRNAs) were prepared by in vitro transcription of rotavirus single-shelled particles and purified by lithium chloride precipitation (Flores, et al supra.). [α-$^{32}$P]GTP was included during the transcription reaction. The specific activity was $5 \times 10^4$ cpm/μg of RNA for those probes tested in liquid hybridization and $5 \times 10^5$ cpm/μg for those used in Northern blot hybridization. The integrity of all 11 RNA segments in each probe was assessed by electrophoresis in 1.4% low melting-temperature agarose gels containing 0.1% sodium dodecyl sulfate (SDS).

Northern blot hybridization:

Genomic dsRNAs from each of the strains were blotted onto diazobenzyloxymethyl (DBM)-paper in a manner similar to that described by Street et al (1982) *J. Virol.* 43:369-378. The dsRNAs were initially run in 6% discontinuous polyacryalminde gels with a 3% stacking gel. The gels were stained with ethidium bromide, photographed, and then immersed in 0.1M NaOH for 20 min to denature and partially break up the RNA and thus facilitate transfer. The NaOH was neutralized and the gels were then transferred by electrophoresis onto freshly prepared DBM membranes (Schleicher & Shuell, Inc., Keen, N.H.) during 4 h at 2A in a transblot unit (Bio-Rad Laboratories, Richmond, Calif.). The membranes were then baked for 2 H at 80° C. and stored at −70° C.

The $^{32}$P-labeled ssRNA probes ($0.5 \times 10^6$ to $1 \times 10^6$ cpm were hybridized to the blotted RNAs following the procedure of Thomas (1980) *Proc. Natl. Acad. Sci. USA* 77:5201-5205. Initially the blotted membranes were incubated for 2 h in a solution containing 2.5 to $5 \times$SSC ($1 \times$SSC=0.15M NaCl plus 0.015M sodium citrate), 50 mM NaPO$_4$ buffer (pH 6.5, 0.1% SDS, 0.02% bovine serum albumin, 0.02% polyvinylpyrrolidone, 0.02% Ficoll (Pharamacia, Inc., Piscataway, N.J.), and 50% formamide. During a second 2-h prehybridization period, blots were incubated in a similar solution also containing 100 μg of sheared and denatured salmon sperm DNA per ml. The salmon sperm DNA as well as the RNA probes were boiled for 5 min and quenched on ice for 5 min before being used. Next, hybridization with the RNA probes was carried out for 20 to 30 h in the latter solution to which dextran sulfate (Pharamacia) was added to concentration of 10%. Following hybridization, the membranes were washed four times at room temperature (about 22° C. to 27° C.) in $1 \times$SSC-0.1% SDS, twice at the temperature used for hybridization (at either 42° or 52° C.) in $2 \times$SSC-0.1%, SDS, and twice in $1 \times$SSC at the temperature used for hybridization. The membrane could be reused by removing the probes during a 30-min wash at 80° C. in 50% formamide-$0.1 \times$SSC-0.1%SDS.

Two different stringencies were used for hybridization in the analysis of corresponding genes of the eight strains under study. Under conditions of low stringency, hybridization was performed at 42° C. with 50% formamide in $5 \times$SSC (0.75M Na$^+$), while under conditions of high stringency, hybridization was performed at 52° with 50% formamide and $2.5 \times$SSC (0.375M Na$^+$). Under these conditions the effective hybridization temperatures were T$_m$ (RNA) −44° C. and T$_m$ (RNA) −29° C., respectively.

Hybridization in solution:

Total (about 0.2 μg) or individually isolated genomic dsRNA segments (approximately 50 ng) were mixed with the $^{32}$P-labeled transcription probes (30 to 60 ng or 1,500 to 3,000 cpm) and denatured by boiling for 2 min, followed by quenching on ice for 5 min. Hybridization was then allowed to occur during overnight incubation at 65° C. in a buffer containing 50 mM Tris acetate (pH 8.0), 250 mM NaCl, and 0.2% SDS. Following hybridization the RNAs were precipitated with ethanol and electrophoresed in discontinuous polyacrylamide gels. The gels were visualised by ethidium bromide and then dried and autoradiographed. Two nursery strains, 1076 and McN, grew poorly in tissue culture, and it was not possible to produce sufficient labeled single-strand probes for all of the desired liquid hybridization experiments.

Relationships among illness and asymptomatic infection rotavirus strains studied by Northern blot hybridization:

Genomic dsRNAs from the eight strains tested, four from newborn infants who underwent silent infection (nursery strains) and four from infant and young children with diarrhea, were resolved by polyacrylamide gel eletrophoresis (PAGE) and blotted onto DBM membranes. Transcription probes from Wa, DS1, P, VA-70, M37 and ST3 were first hybridized to these blots at low stringency (42° C., 50% formamide, 5×SSX). Homologous hybridizations were performed in each instance to confirm the integrity of the transcription probes. Under these conditions of hybridization, the eight strains could not be differentiated (data not shown). In tests with every strain, each segment which could be resolved by PAGE gave a positive signal with the corresponding ssRNA of each of the probes. In some case it was not possible to resolve segments 2 and 3 or 7,8 and 9 because the segments migrated very closely together.

Figure 2:
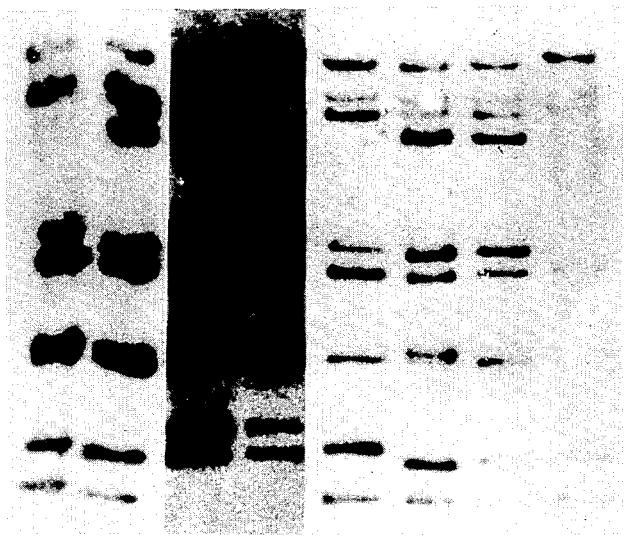
FIG. 2 shows autoradiogram of Northern blot hybridization at a higher stringency of $^{32}$P-labeled asymptomatic neonatal rotavirus M37 (top) and asymptomatic neonatal rotavirus ST3 (bottom) ssRNA probes to denatured genomic RNAs from the following rotavirus strains immobilized on DBM membranes after PAGE: lane 1, virulent human rotavirus WA; lane 2, asymptomatic neonatal rotavirus M37; lane 3, virulent human rotavirus DS1; lane 4, asymptomatic neonatal rotavirus 1076; lane 5, virulent human rotavirus P; lane 6, asymptomatic neonatal rotavirus McN; lane 7, asymptomatic neonatal rotavirus ST3; lane 8, virulent human rotavirus VA70. o identifies strains recovered from asymptomatic newborn infants. Lanes 3 and 4 were exposed for a longer period of time.
Figure 2:
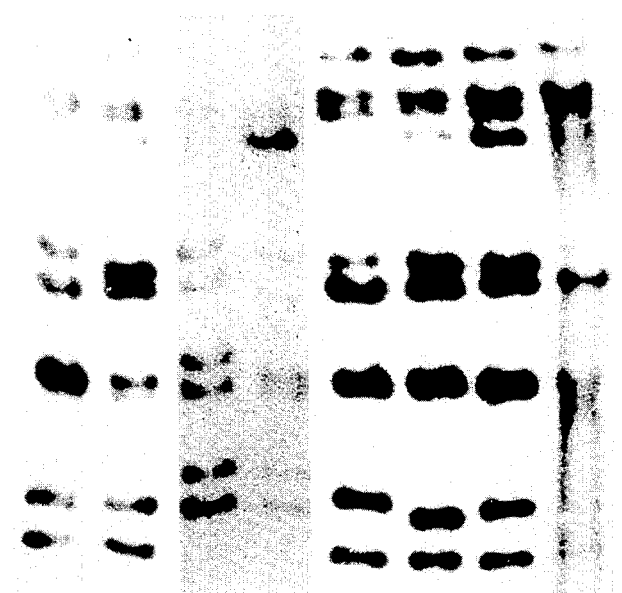

Hybridization at a higher stringency (52° C., 50% formamide, 2.5×SSC) was also performed with probes from each of the eight strains (FIGS. 1 and 2). All of the pairwise comparisons were performed by Northern blot at a higher stringency in both directions. Again, homologous hybridizations were included to confirm the integrity of the transcription probes (shown in FIG. 1 lane 1 under Wa probe, and FIG. 2 lane 3 under DSI probe). Strains obtained from symptomatic infants and young children (Wa, DS1, P and VA70) clearly hybridized with every segment that was resolved from the eight strains which were blotted, with the exception of the fourth segment from the strains which were recovered from asymptomatic newborn infants (M37, 1076, McN, and ST3). The fourth segment of the latter viruses failed to produce a signal or produced a very faint signal compared with that produced by the other gene segments. Examples of these patterns with ssRNA probes from Wa and DS1 are shown in FIG. 1.

Similarly, probes from the nursery strains, M37, 1076, McN and ST3, failed to hybridize (or hybridized faintly) to the fourth segment of strains recovered from symptomatic infants and young children (Wa, DS1, P, and VA70), while these probes reacted with each of the other gene segments of these strains which could be clearly resolved by PAGE. The results obtained with probes from M37 and ST3 are shown in FIG. 2; probes from 1076 and McN yielded similar results. In every instance probes prepared from each of the four nursery strains hybridized strongly to the fourth gene of the other three nursery strains. The nursery strain probes also hybridized to all of the other heterotypic nursery strain genes which could be resolved by PAGE.

Probes prepared from Wa, P, VA70, M37, McN and ST3 (members of the Wa family of human rotaviruses, [Flores, et al, (1982), *Infect. Immun.* 37:648,655]) hybridized less strongly to the first three genes of DS1 and 1076 (members of the DS1 family of human rotaviruses [Flores et al supra.]) than to the corresponding genes of viruses in the former group (shown in FIGS. 1 and 2, lanes 3 and 4 for Wa, M37, and ST3; similar results were obtained with McN and VA70). Conversely, probes prepared from DS1 and 1076 hybridized less strongly to the first three genes of Wa family viruses than to 1076 or DS1 (lanes 1 and 2 and 6 through 8 at the bottom of FIG. 1 for DS1 probe; similar results were observed with the 1076 probe).

Thus, a hierarchy of hybridization reactions was observed. Probes for genes 5 through 11 hybridized strongly with the corresponding genes of all other strains. Probes from Wa or DS1 family virus also hybridized strongly with the first three genes of the other viruses in their family group, while reactions were less intense with the first three genes of viruses belonging to the other family. Finally, the fourth genes of the illness strains hybridized strongly among themselves but not with the corresponding genes of the nursery strains and vice versa. The degree of hybridization observed between the fourth genes of the illness and nursery strains were clearly less than that seen between the first three genes of the Wa and DS1 family viruses. Thus, the fourth genes of the nursery strains appear to be highly related and distinct from the corresponding genes of the illness strains. The latter genes also appear to be highly related when assayed by Northern blot hybridization. Clearly, the observed conservation of the fourth gene among nursery strains and among illness strains is independent of the serotype or Wa/DS1 family relationship.

Figure 3:
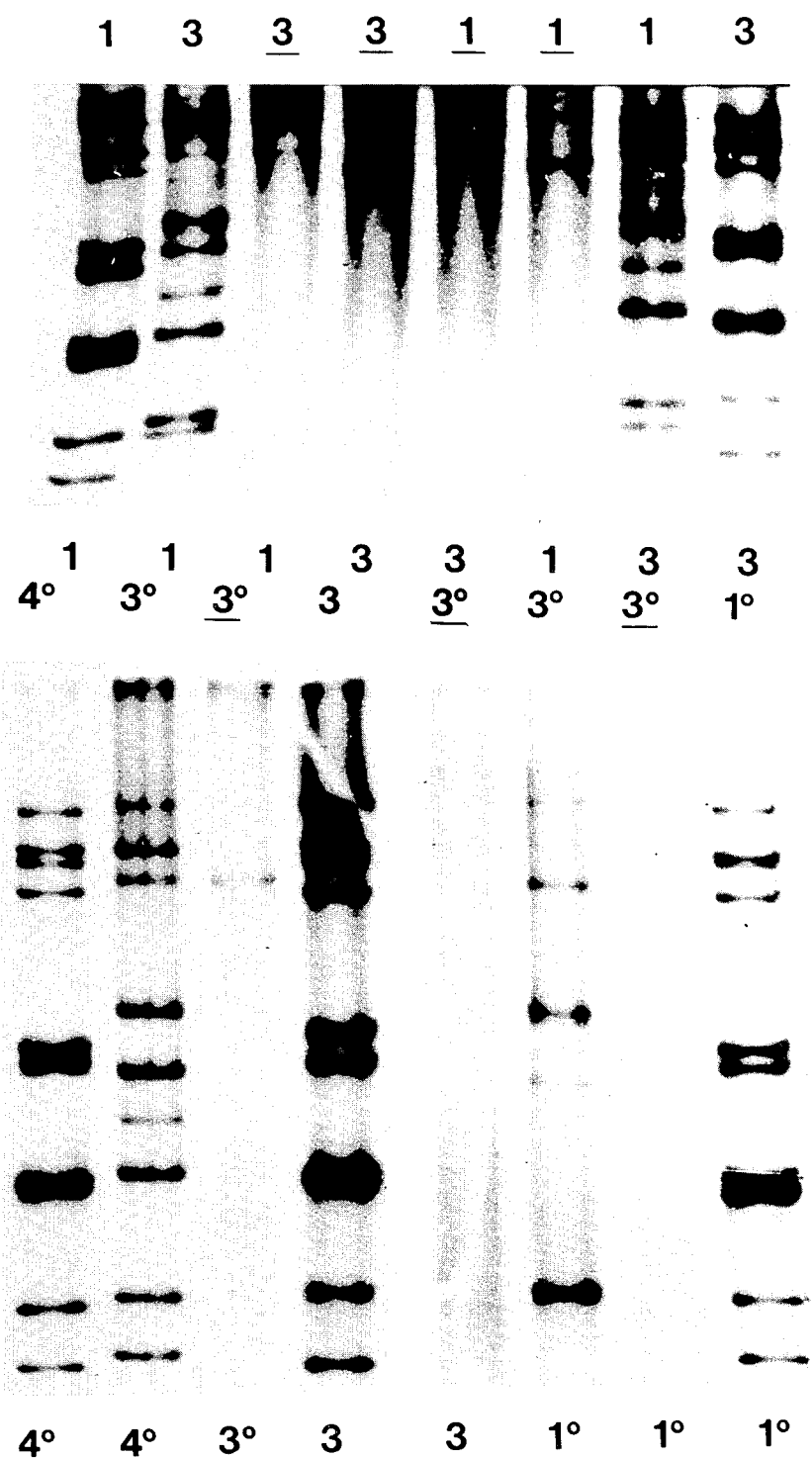
FIG. 3 shows hybridization of denatured genomic RNAs from several rotavirus strains to $^{32}$P-labeled ssRNA probes. Hybridizations were carried out in solution (overnight incubation at 65° C.), and the RNAs were electrophoresed in 10% acrylamide gels, dried, and autoradiographed. Number on top of each lane identifies pairwise hybridization (dsRNA-ssRNA probe, in that order) as follows: (top)-(1) Wa/Wa;(2)P-/Wa;(3) isolated gene 4 from P/Wa; (4) isolated gene 4 from P/P; (5) isolated gene 4 from Wa/P; (6) isolated gene 4 from Wa/Wa;(7)Wa/P; (8) P/P (bottom)-(1)ST3/ST3;(2)McN/ST3; (3) isolated gene 4 from McN/ST3; (4) P/P; (5) isolated gene 4 from McN/P; (6) McN/M37; (7) isolated gene 4 from McN/M37; (8) M37/M37.
Figure 4:
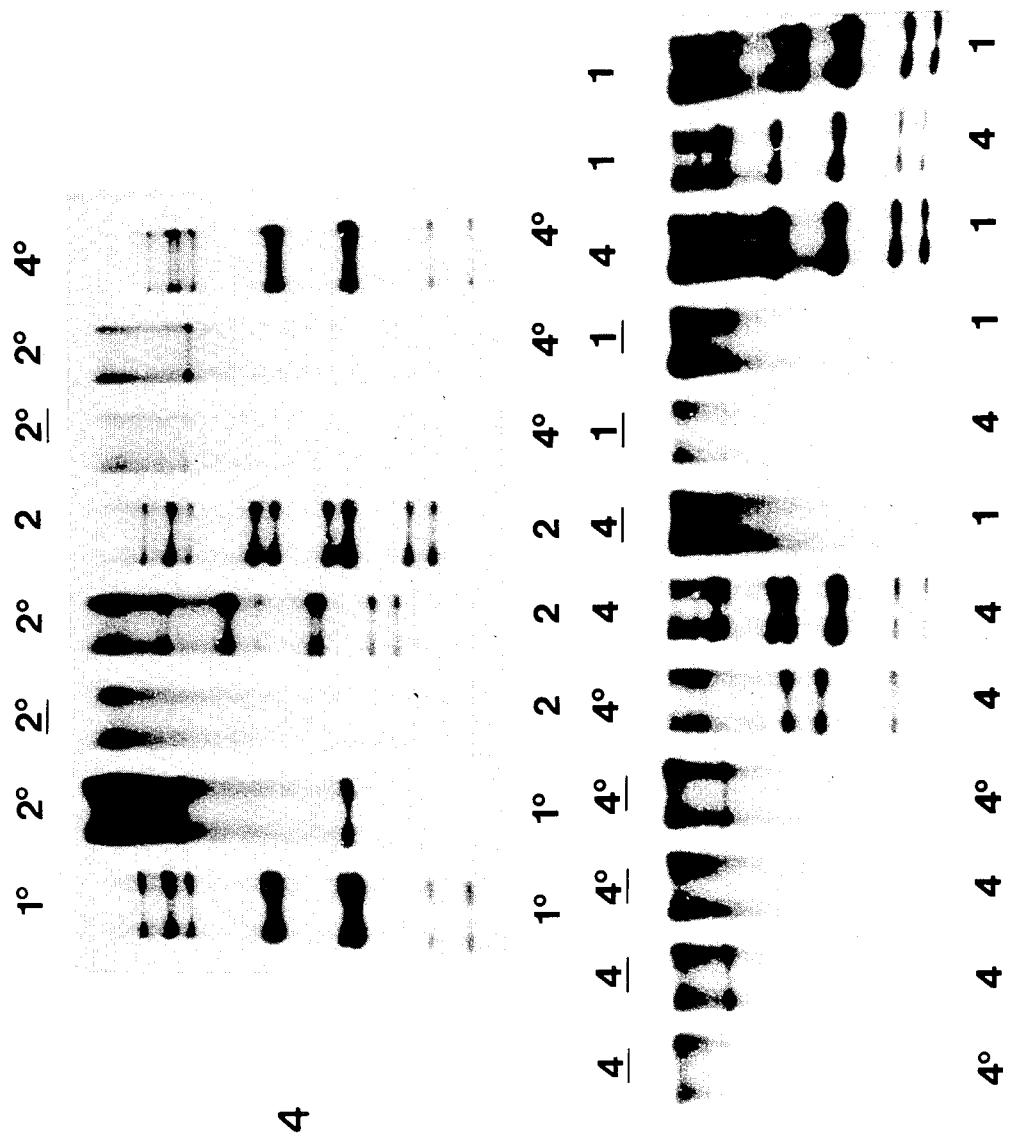
FIG. 4 shows hybridization of denatured genomic RNAs from several rotavirus strains to $^{32}$P-labeled ssRNA probes. Hybridizations were carried out in solution (overnight incubation at 65° C.), and the RNAs were electrophoresed in 10% acrylamide gels, dried, and autoradiographed. Number on top of each lane identifies pairwise hybridization (dsRNA/ssRNA probe in that order as follows: (top)-(1) M37/M37; (2)1076/M37; (3) isolated gene 4 from 1076/DS1; (4) 1076/DS1; (5) DS1/DS1; (6) isolated gene 4 from 1076/ST3; (7) 1076/ST3; (8) ST3/ST3; (bottom)-(1) isolated gene 4 from VA70/ST3; (2) isolated gene 4 from VA70/VA70; (3) isolated gene 4 from ST3/VA70; (4) isolated gene 4 from ST3/ST3; (5) ST3/V70; (6) VA70/VA70; (7) isolated gene 4 from VA70/Wa; (8) isolated gene 4 from Wa/VA70; (9) isolated gene 4 from Wa/Wa; (10) VA70/Wa; (11) Wa/VA70; (12) Wa/Wa.

Relationship among the fourth genes of illness and asymptomatic infection rotavirus strains studied by hybridization in solution:

Total genomic RNAs from all strains were denatured and hybridized to transcription probes in solution. The resulting hybrids were analyzed by PAGE, fluorography, and autoradiography. Homologous hybridizations were included in each experiment to establish the integrity of the probes. In many cases, certain of the hybrids which formed between ssRNA probes and denatured genomic dsRNAs of other strains could not be identified because their migration pattern on PAGE differed from that of the corresponding genes of both viruses being compared. Thus, to extend to the analysis of relatedness among the fourth genes of the strains under study, it was necessary in certain instances to isolate and extract gene 4 by preparative gel electrophoresis. The isolated gene was then denatured and hybridized to transcription probes. Examples of this procedure are shown in FIGS. 3 and 4 and a summary of the results obtained by this approach is presented in Table 1.

TABLE 1

Relationship of fourth genes of various rotaviruses as studied by Northern blot and hybridization in solution

| Recovery from: | Strain from which $^{32}$P-labeled ssRNA transcription probe was prepared | | Hybrid formation when indicated denatured ds genomic RNA(s) incubated with labeled transcription probe Northern blot (higher stringency) | | | | | | | |
|---|---|---|---|---|---|---|---|---|---|---|
| | Designation | Serotype | Wa | DS1 | P | VA70 | M37 | 1076 | McN | ST3 |
| Ill infants | Wa | 1 | ⊞$^a$ | + | + | + | 0 | 0 | 0 | 0 |
| | DS1 | 2 | + | ⊞ | + | + | ± | 0 | 0 | 0 |
| | P | 3 | + | + | ⊞ | + | 0 | 0 | 0 | 0 |

TABLE 1-continued

Relationship of fourth genes of various rotaviruses as studied by Northern blot and hybridization in solution

|  |  |  |  |  |  |  |  |  |  |  |
|---|---|---|---|---|---|---|---|---|---|---|
|  | VA70 | 4 | + | + | + | ⊞ | 0 | 0 | 0 | 0 |
| Asymptomatic newborn infants | M37 | 1 | 0 | 0 | 0 | 0 | ⊞ | + | + | + |
|  | 1076 | 2 | 0 | 0 | ± | 0 | + | ⊞ | + | + |
|  | McN | 3 | 0 | 0 | 0 | 0 | + | + | ⊞ | + |
|  | ST3 | 4 | 0 | 0 | 0 | 0 | + | + | + | ⊞ |

|  | Strain from which $^{32}$P-labeled ssRNA transcription probe was prepared | | Hybrid formation when indicated denatured ds genomic RNA(s) incubated with labeled transcription probe Hybridization in soln and analysis by PAGE | | | | | | | |
|---|---|---|---|---|---|---|---|---|---|---|
| Recovery from: | Designation | Serotype | Wa | DS1 | P | VA70 | M37 | 1076 | McN | ST3 |
| Ill infants | Wa | 1 | ⊞$^b$ | 0 | +$^b$ | +$^b$ | 0$^b$ | 0 | 0 | 0 |
|  | DS1 | 2 | 0 | ⊞ | 0 | 0 | 0 | 0$^b$ | 0 | 0 |
|  | P | 3 | +$^b$ | 0 | ⊞$^b$ | 0$^b$ | 0 | 0 | 0$^b$ | 0$^b$ |
|  | VA70 | 4 | +$^b$ | 0 |  | ⊞$^b$ | 0 | 0 | 0 | 0$^b$ |
| Asymptomatic newborn infants | M37 | 1 | 0$^b$ | 0$^b$ | 0$^b$ | 0$^b$ | ⊞$^b$ | +$^b$ | +$^b$ | +$^b$ |
|  | 1076 | 2 |  |  |  |  |  |  |  |  |
|  | McN | 3 |  |  |  |  |  |  |  |  |
|  | ST3 | 4 | 0$^b$ | 0 | 0 | 0$^b$ | +$^b$ | +$^b$ | +$^b$ | ⊞$^b$ |

$^a$Homologous reaction boxed.
$^b$Hybridization also performed with denatured genomic RNA of isolated gene 4.

The top portion of FIG. 3 shows the pattern observed when the total genomic dsRNAs or only the fourth gene from Wa and P were cross-hybridized to probes from these strains. A hybrid formed between the fourth genes of Wa and P which had an electrophoretic mobility different from the fourth gene of either strain. The fourth gene of Wa also hybridized under these conditions to the fourth gene of VA70 (FIG. 4) but it did not hybridize to the fourth gene of DS1 or either of the nursery strains tested, M37 or ST3 (not shown).

The bottom of FIG. 3 shows the hybrids which formed between denatured dsRNAs of McN and probes from ST3 and M37. The fourth gene of the nursery strain McN formed hybrid bands with the corresponding gene from nursery strains ST3 and M37, and these hybrids exhibited the same pattern of migration as that of McN. However, the fourth gene of McN did not form a hybrid with P, a strain recovered from an ill child.

FIG. 4 (top) shows the hybrids which formed between denatured RNAs from the nursery strain 1076 and probes from M37 and DS1. A homologous DS1/DS1 or M37/M37 hybridization established the integrity of the DS1 and M37 probes. Total genomic RNAs from 1076 formed a series of hybrid bands with a DS1 probe (lane 4); however, none of the hybrids corresponded to the fourth gene since the isolated fourth gene of 1076 did not form a hybrid segment with the DS1 probe (lane 3). In contrast, the fourth gene of strain 1076 formed a hybrid band with the M37 probe (lane 2). Pairwise comparison of three of the nursery strains (M37, 1076, and ST3) was of particular interest because only the fourth genes of the 1076 and ST3 appeared to be closely related, while only two genes of M37 and 1076 appeared to be closely related (the fourth and seventh genes).

The bottom of FIG. 4 shows the hybrids which formed between VA70 and ST3 (both serotype 4 strains) and between WA and VA70. Although ST3 and VA70 formed at least seven hybrid bands, their fourth genes did not hybridize. The fourth gene of VA70, on the other hand, did form a hybrid with the fourth genes of Wa, and this hybrid exhibited the same mobility as the Wa fourth gene.

A summary of the liquid hybridization analysis of the fourth genes of the eight strains tested is presented in Table 1, which contains observations not included in FIGS. 3 and 4. Gene 4 of nursery strain M37 or ST3 formed a full-length hybrid with the corresponding gene of each of the other three nursery strains isolated from infants without diarrheal illness (Table 1). A less consistent pattern of full-length hybrid formation was observed in pairwise tests of illness strains. No illness strain probe formed a full-length gene 4 hybrid with every one of three other illness-strains. Full-length gene 4 hybrid formation was observed in two of three pairwise tests with the Wa strain probe, in one of three crosses with the P or VA70 strain probe, and in none of three instances with the DS1 strain probe. Significantly, full length gene 4 hybrids were not observed in any of the pairwise tests of illness versus nursery strains.

It should be noted that hybridization in solution proved to be a more stringent test for homology because seven of the pairwise comparisons that were positive by Northern blot (high-stringency) analysis were not positive by the former procedure. In no instance, however, was a pairwise comparison positive by liquid hybridization and negative by Northern blot.

Relationships among the remaining 10 genes of illness and asymptomatic infection rotavirus strains studied by hybridization in solution:

Previously it had been observed that the majority of genes of most human rotaviruses produced full-length hybrids when tested with labeled transcripts from the Wa strain but not when tested with transcripts from the DS1 strain or vice versa (Flores, et al supra). This suggested that most human rotaviruses belonged to the Wa or DS1 family of viruses. The relationship of the genes of each of the illness and nursery strains, other than gene 4, to the corresponding genes of the Wa and DS1 strains is summarized in Table 2. In all but one instance, hybridization was observed with only one of the two probes tested, Wa or DS1. The exception was the M37 strain, which produced seven hybrids with the Wa probe and one with the DS1 probe. Three of the illness strains and three of the nursery strains belong to the Wa family, while a single illness strain and a single necessary strain belonged to the DS1 family. Significantly, both of the DS1 family viruses shared the same subgroup and serotype, while the six Wa family viruses shared another subgroup and represented three different serotypes. Thus, conservation of gene 4 among nursery strains was observed independent of Wa or DS1 family relationship as well as of subgroup and serotype.

Relationships among the remaining 10 genes of the asymptomatic infection strains studied by hybridization in solution:

As expected, the 10 remaining genes of the three nursery strains that belonged to the Wa family and subgroup 2 exhibited a closer relationship to each other than to the corresponding genes of the DS1-like, subgroup 1 rotavirus, strain 1076 (Table 3). Again, these relationships among the non-gene 4 RNA segments were observed independent of the conservation of gene 4 by the four nursery strains.

TABLE 2

Relationship of rotaviruses recovered from ill patients or asymptomatic newborns to Wa and DS1 prototype rotaviruses by liquid hybridization and PAGE[a]

| | No. of hybrids other than gene 4 detected by a liquid hybridization and PAGE with indicated labeled ssRNA transcripts from: | | |
|---|---|---|---|
| Rotavirus | Wa | DS1 | Comment |
| Ill patients | | | |
| Wa (serotype 1) | 10 | 0 | Wa family prototype |
| DS1 (serotype 2) | 0 | 10 | DS1 family prototype |
| P (serotype 3) | 9 | 0 | Predominantly Wa-like |
| VA70 (serotype 4) | 7 | 0 | Predominantly Wa-like |
| Asymptomatic newborn infants | | | |
| M37 (serotype 1) | 7 | 1 | Predominantly Wa-like |
| 1076 (serotype 2) | 0 | 8 (9?) | Predominantly DS1-like |
| McN (serotype 3) | 8 | 0 | Predominantly Wa-like |
| ST3 (serotype 4) | 7 | 0 | Predominantly Wa-like |

[a]Because comigration of genes 2 and 3 and genes 7,8, and 9 often occurs, the number of full-length hybrids listed may represent a minimal estimate of relatedness between viruses except in instances in which hybrids were not detected.

TABLE 3

Liquid cross-hybridization among rotaviruses from asymptomatic newborn infants

| | Full-length hybrids other than gene 4 detected by liquid hybridization and PAGE of indicated melted ds genomic RNAs and labeled ssRNA transcripts[a] | | |
|---|---|---|---|
| Rotavirus strain | 1076 | McN | ST3 |
| M37 | 1(7th gene) | 4 | 6 |
| 1076 | | ND[b] | 0 |
| McN | | | 9 |

[a]Because comigration of genes 2 and 3 and genes 7, 8 and 9 often occurs, the number of full-length hybrids listed may represent a minimal estimate of relatedness between viruses except in instances in which hybrids were not detected.
[b]ND. Not done.

As shown herein the RNA-RNA hybridization analysis reveals a major difference between the asymptomotatic nursery strains and rotavirus strains isolated from infants and children with gastroenteritis. Namely, the fourth gene of the nursery strains failed to hybridize under conditions of high stringency (Northern blot or liquid hybridization) to the corresponding gene of strains recovered from ill infants and children. This difference was independent of the serotype specificity of these viruses. Thus, each of the four nursery strains, which represented four separate serotypes, failed to form a gene 4 hybrid with a rotavirus strain of the same serotype recovered from an ill individual. In contrast, the fourth gene of the four strains from anymptomatic newborns was highly conserved despite serotype polymorphism.

When studied by Northern blot analysis, under conditions of high stringency, the fourth genes of the illness strains constituted a conserved group in which hybridization occurred in each pairwise test, while hybridization was not detected with the fourth gene of any of the nursery strains. The fourth genes of the nursery strains also constituted a conserved group in which cross-hybridization occurred, while hybridization with the fourth gene of illness strains was not detected. In tests in which liquid hybridization, a more stringent technique, was used with two nursery strain probes, M37, and ST3, and the four illness strain probes, the fourth gene of the nursery strains was also observed to be highly conserved. Full-length gene 4 hybrids were detected in each instance when the nursery strains were tested with the former probes but not with the latter probes. The fourth gene of each of the illness strains did not form full-length hybrids with the two nursery strain probes. The nursery strain probes, however, did form full-length gene 4 hybrids with each of the heterotypic nursery strains. Significantly, the fourth genes of the illness strains exhibited less conservation when studied by liquid hybridization in pairwise tests than was evident by the less stringent Northern blot analysis. Thus, the fourth genes of the nursery strains appeared to be a more closely related group than the fourth genes of the illness strains.

The observations just described also indicate that the difference in virulence of the nursery and illness strains results, in part, from a difference in the fourth gene product of these two groups of rotaviruses. The fourth rotavirus gene encodes VP3, an 88,000-dalton outer capsid rotavirus protein which must be cleaved by trypsin or another peptidase for virus to become infectious in vitro or in vivo (Estes, et al (1981) *J. Virol.* 39:879-888). Genetic studies also indicate that the fourth rotavirus gene product is important in determining host range of rotavirus in tissue culture. Initially, it was observed that noncultivatable human rotavirus strains could be rescued by gene reassortment with an animal rotavirus that grew well in vitro. These studies established that the fourth gene of human rotaviruses restricted growth in vitro and that its replacement with the corresponding gene of a cultivatable bovine rotavirus, strain UK, made it possible for human rotavirus reassortants to grow efficiently in vitro (Flores, et al supra. and Kalica, et al (1981) *Virology* 13:22-29). Presumably restriction of host range in vitro is related to a deficiency of the appropriate proteolytic enzyme(s) in tissue culture cells and the ease with which cleavage of VP3 occurs in vitro.

Processing of VP3, the fourth gene product, by those proteolytic enzymes which are most abundant during the neonatal stage of intestinal maturation may allow nursery rotaviruses to replicate to a moderate level without causing disease. On the other hand, neonatal intestinal enzymes may not activate strains which are able to infect and produce illness in older infants and children. Also, nursery strains may not cause diarrhea in older infants and children because cleavage of VP3 by "mature" proteolytic enzymes may not be efficient. However, it is unlikely that these strains only infect the newborn. Unfortunately, there have been no attempts to recover rotavirus strains from asymptomatic older infants and children.

The role of the fourth gene product in the neutralization of rotaviruses has been the subject of several recent studies. Greenberg et al J. Virol 47:267–275, generated neutralizing monoclonal antibodies that reacted with VP3. Hoshino et al (1985) Proc. Natl. Acad. Sci. USA 82;8701–8704, discovered that certain rotaviruses, for example the nursery strain M37 analyzed in this study, exhibited two distinct serotypes. Thus, antibodies against strain M37 neutralize serotype 1 strains, such as Wa, as well as nursery strain ST3, a serotype 4 rotavirus. This intertypic neutralization phenomenon was mapped to the outer capsid VP7 protein of M37 and Wa and to another outer capsid protein, VP3, of M37 and ST3. The latter relationship is of interest because of the M37 VP3 gene cross-hybridizes with the VP3 gene of ST3 under conditions of high stringency. It is noted that intertypic neutralization such as that observed for M37 and ST3, was not detected with the other nursery strains included in this study (1076, McN) although all of the nursery strains share a high level of homology in their fourth gene. In a similar manner, the fourth gene of Wa exhibited a high degree of homology with the corresponding gene of strains P and VA70, which belong to different serotypes and do not exhibit intertypic neutralization with Wa or with each other. Given that the fourth gene product is capable of inducing neutralizing antibodies, it is likely that the epitopes responsible for inducing neutralizing antibodies represent a small portion of the total VP3 and hence may not exert a significant influence on hybridization of gene 4 RNAs.

When performing RNA-RNA hybridizations in solution a high degree of homology among many genes other than gene 4 was detected in various crosses. The hybridization conditions used in this assay were rather stringent, since RNA-RNA annealing was allowed to occur at a high temperature which destablizes partial hybrids with >18% mismatch. The actual degree of homology required to form a stable hybrid was demonstrated by sequence analysis to be even greater, ≧92% (Gorziglia, et al (1986) Proc. Natl. Aca. Sci. USA 83:7039–7043). In addition, the migration pattern of partial hybrids was altered with respect to that of the genes from which they originated. Nevertheless, the hybridization patterns observed were consistent with a previous observation that most human rotaviruses studied by liquid hybridization can be classified in one of two major families, one with relatively high homology to Wa and the other with significant homology to DS1 (Flores, et al (1982) Infect Immun 37:648–655 and Flores et al. (1985) J. Med. Virol. 17:135–143). In the present study this dichotomy was maintained independent of the origin of the strains, whether from asymptomatic newborns or symptomatic infants and children. Without being bound to any specific theory, it is postulated that illness and nursery strain genes other than gene 4, may have common origin and may be derived from one of two distinct ancestral sources, a Wa-like virus or a DS1-like virus. Particularly instructive in this regard was the analysis of three nursery strains, M37, 1076 and ST3. Strain 1076 shared a high degree of homology with only gene 4 of ST3 and genes 4 and 7 of M37. On the other hand, 1076, exhibited significant homology with at least eight or nine genes of DS1, the protype of the DS1 family, while at least seven of the genes of M37 and ST3 appeared to be highly related to the corresponding genes of the Wa strain. These observations suggest that strain 1076 may have arisen through gene reassortment involving virus bearing a nursery strain gene 4 and a virus with predominantly DS1-like genes. A similar origin can be suggested for the M37 and ST3 viruses, but in these instances gene reassortment probably occured with a virus which was Wa-like.

Marked conservation of sequence among the fourth genes of the nursery strains identified by RNA-RNA hybridization was further evaluated by determining and comparing the nucleotide sequence of the region of the fourth gene of virulent as well as asymptomatic human rotaviruses that codes for the VP8 protein, downstream cleavage sites and the N terminus of VP5 (Gorziglia et al., Proc. Nat. Acad. Sci. (1986), pp. 7049,7043). The fourth segment (+) strand RNA was found to have a 5' conserved nontranslated sequence of 9 nucleotides and encoded a VP8 protein of 240 amino acids in human rotavirus strains. Alignment of amino acid sequences of the VP8 protein, the downstream cleavage region and the N-terminus of VP5 of asymptomatic and virulent human rotavirus strains indicated a high degree of homology (96% or more) among the asymptomatic rotaviruses (serotypes 1, 2, 3, and 4), while homology between asymptomatic rotavirus strains and virulent rotaviruses was considerably less (68–72%) (Table 4). Amino acid homology for virulent and asymptomatic human rotavirus strains within the same serotype also ranged from 68% to 72%. A high degree of conservation of amino acid sequence (92–97%) was also observed among 3 of the virulent strains (serotypes 1, 3, and 4). At 48 positions in the protein sequence of VP8, the cleavage region and the N terminus of VP5, an amino acid was conserved among asymptomatic rotaviruses, while a different amino acid was conserved among virulent rotaviruses (Table 5 and FIG. 5). Notably, three of these differences were located within the cleavage region between VP8 and VP5. These observations confirmed the conservation of sequence within the fourth gene of the rotaviruses recovered from newborns who underwent asymptomatic infection. These findings also suggested that the fourth genes of virulent and asymptomatic human rotavirus strains represent two lines of divergent evolution from a common ancestor. It is likely that this sequence dimorphism may be responsible in part for the difference in virulence between these two groups of human rotaviruses.

TABLE 4

PERCENT AMINO ACID (OR NUCLEOTIDE) HOMOLOGY IN VP8 AND N TERMINUS OF VP5 AMONG FOUR VIRULENT AND FOUR ASYMPTOMATIC HUMAN ROTAVIRUS STRAINS

| Rotavirus | Wa | DS-1 | P | VA70 | M37 | 1076 | McN | ST3 |
|---|---|---|---|---|---|---|---|---|
| Virulent human RV | | | | | | | | |
| Wa (Serotype 1) | — | 85(86) | 95(94) | 96(97) | 69(71) | 70(72) | 70(72) | 69(72) |
| DS-1 (Serotype 2) | | | 89(86) | 86(86) | 70(71) | 70(72) | 70(71) | 68(71) |
| P (Serotype 3) | | | | 94(92) | 69(71) | 70(72) | 70(72) | 69(71) |
| VA70 (Serotype 4) | | | | | 71(72) | 72(73) | 72(73) | 71(73) |
| Asymptomatic human RV | | | | | | | | |
| M37 (Serotype 1) | | | | | — | 96(96) | 97(97) | 96(97) |

TABLE 4-continued
PERCENT AMINO ACID (OR NUCLEOTIDE) HOMOLOGY IN VP8 AND N TERMINUS OF VP5 AMONG FOUR VIRULENT AND FOUR ASYMPTOMATIC HUMAN ROTAVIRUS STRAINS

| Rotavirus | Wa | DS-1 | P | VA70 | M37 | 1076 | McN | ST3 |
|---|---|---|---|---|---|---|---|---|
| 1076 (Serotype 2) | | | | | | | 99(98) | 97(97) |
| McN (Serotype 3) | | | | | | | | 98(98) |
| ST3 (Serotype 4) | | | | | | | | |

TABLE 5
CONSERVATION OF DIFFERENT AMINO ACID SEQUENCES IN VP8, THE CLEAVAGE REGION AND THE N TERMINUS OF VP 5 OF ASYMPTOMATIC AND VIRULENT ROTAVIRUSES

| Position at which aa sequence is conserved in asymptomatic and in virulent rotaviruses | Amino acid present in rotavirus strains | | Position at which aa sequence is conserved in asymptomatic and in virulent rotaviruses | Amino acid present in rotavirus strains | |
|---|---|---|---|---|---|
| | Asymptomatic (N = 4) | Virulent (N = 4) | | Asymptomatic (N = 4) | Virulent (N = 4) |
| Amino acid no. 17 | Glu | Asp | Amino acid no. 154 | Lys | Arg |
| 19 | Ser | His | 162 | Lys | Arg |
| 23 | Asn | Glu | 164 | Ala | Val |
| 24 | Thr | Gln | 170 | Tyr | Gly |
| 44 | Asn | Arg | 171 | Asn | Gly |
| 49 | Val | Asn | 172 | Ser | Arg |
| 50 | Leu | Trp | 182 | His | Arg |
| 51 | Glu | Gly | 187 | Tyr | Ser |
| 55 | Val | Ile | 191 | Ser | Ala |
| 73 | Ser | Thr | 194 | Ser | Asn |
| 84 | Leu | Ile | 195 | Glu | Asn |
| 86 | Pro | Ser | 196 | Val | Ile |
| 87 | Thr | Asn | 197 | Glu | Ser |
| 89 | Gln | Asn | 198 | Thr | Ile |
| 90 | Gln | Gly | 202 | Val | Ser |
| 93 | Leu | Tyr | 221 | Thr | Asn |
| 95 | Gly | Ser | 226 | Met | Ile |
| 98 | Lys | Asn | 232 | Ile | Val |
| 101 | Ile | Phe | 235 | Val | Leu |
| 105 | Leu | Val | 242 | Val | Ile |
| 111 | Asn | His | 243 | Thr | Gln |
| 128 | Ile | Phe | 245 | Gln | Lys |
| 129 | Thr | Asn | 277 | Asn | Gly |
| 147 | Val | Ser | | | |
| 148 | Ser | Gln | | | |

In summary, the results presented herein clearly demonstrate a distinctive difference in gene 4 sequence between strains recovered from asymptomatic newborn infants ("nursery strains") and strains recovered from infants and young children with diarrhea. Although the nursery strains exhibited serotypic diversity (i.e., each of the four strains tested belonged to a different serotype), the fourth gene appeared to be highly conserved. Similarly, each of the virulent strains tested belonged to a different serotype; nonetheless there was significant conservation of sequence among the fourth genes of the three of these viruses. Significantly, the conserved fourth genes of the nursery strains were distinct from the fourth gene of each of the virulent viruses.

Of course, a basic teaching of the present invention, inter alia, is that a critical difference between a virulent and attenuated rotavirus is the presence of the fourth gene in the attenuated rotavirus and the absence of the same in the genome of the virulent strain. Based on this finding of the present invention, any virulent rotavirus, which, due to its virulent nature, cannot be used as an inoculum for making a vaccine, now can be used in the preparation of a vaccine by merely replacing the fourth viral gene segment in the genome of said virulent rotavirus, with the conserved fourth gene fron the naturally attenuated rotavirus strain, thereby converting or rendering the virulent rotavirus attenuated. Of course, insertion of a new gene into a viral genome and isolation of the desired reassortants can be routinely accomplished by the standard techniques of gene reassortment and isolation therefrom of the desired strain by such methods as use of neutralizing antibodies directed against the fourth gene product of the virulent rotavirus and the like, well known to one of ordinary skill in the art to which this invention belongs. A pure inoculum of the reassortant viral strain carrying the fourth gene (either present naturally or derived through genetic reassortment) is then prepared and administered in immunogenic amounts, preferably in a pharmaceutically acceptable, non-toxic carrier, to a host susceptible to rotavirus infection to induce immunization against rotavirus diseases. A suitable route of inoculation well known in the art, such as oral administration, can be resorted to and any suitable carrier such as physiological saline or a non-toxic buffer can be employed for the preparation or administration of a pharmaceutical immunogenic composition.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for producing a vaccine against rotavirus disease, consisting essentially of:
    (a) isolating a rotavirus from humans having undergone asymptomatic rotaviral infection;

(b) analyzing the isolated virus obtained from step (a) by confirming the presence of the desired fourth rotaviral gene associated with rotaviral attenuation;

(c) growing a purified inoculum of the isolated rotavirus, carrying the fourth gene, in cells acceptable for use in vaccine for human administration; and (d) employing an immunogenic amount of the rotavirus infected cells of step (c) as a vaccine in a pharmaceutically acceptable carrier.

2. A method for producing a vaccine against rotavirus disease, consisting essentially of:

(a) constructing a rotavirus by substituting in the genome of a virulent rotavirus strain the fourth rotaviral gene segment associated with rotaviral attenuation by reassortment methodology;

(b) analyzing the isolated virus obtained from step (a) by confirming the presence of the desired fourth rotaviral gene associated with rotaviral attenuation;

(c) analyzing the reassortant obtained from step (b) by conventional methodology including hybridization and sequence analysis to confirm the presence of desired fourth rotaviral gene associated with rotaviral attenuation;

(d) employing an immunogenic amount of the rotavirus infected cells of step (c) as a vaccine in a pharmaceutically acceptable carrier.

(e) employing immunogenic amount of the virus from step (d) as a vaccine in a pharmaceutically acceptable carrier.

* * * * *